United States Patent [19]

Raynolds

[11] 4,307,239
[45] Dec. 22, 1981

[54] PREPARATION OF THIOPHENE COMPOUNDS

[75] Inventor: Peter W. Raynolds, Kingsport, Tenn.

[73] Assignee: Eastman Kodak Company, Rochester, N.Y.

[21] Appl. No.: 182,900

[22] Filed: Sep. 2, 1980

[51] Int. Cl.³ .................................. C07D 333/24
[52] U.S. Cl. ................................ 549/79; 549/76; 549/78; 548/240
[58] Field of Search ............... 549/79, 76, 78; 548/240

[56] References Cited

PUBLICATIONS

J. Org. Chem., 45, No. 4, 617 (1980).

*Primary Examiner*—Alan Siegel
*Attorney, Agent, or Firm*—J. Frederick Thomsen; D. B. Reece, III

[57] ABSTRACT

Disclosed is a process for the preparation of thiophenes having the formula

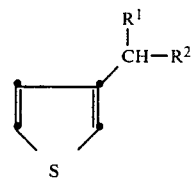

by contacting a compound having the formula

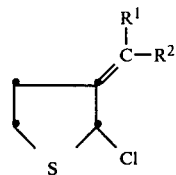

with certain amine bases. Other amine bases can be employed when a two-phase reaction system is used.

7 Claims, No Drawings

PREPARATION OF THIOPHENE COMPOUNDS

This invention pertains to a novel process for the preparation of certain thiophene compounds which can be hydrolyzed to 3-thienylmalonic acid, a compound useful in the preparation of pharmaceuticals.

One embodiment of the process of this invention comprises a process for the preparation of a compound having the formula

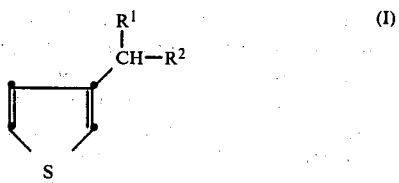

by contacting a compound having the formula

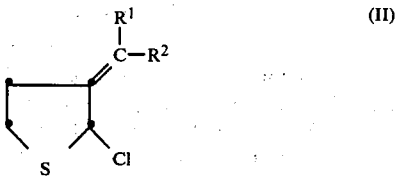

in an inert organic solvent with an amine having a $pK_b$ of about 8 to 10, wherein $R^1$ and $R^2$ are groups hydrolyzable to carboxyl groups. Since it is not necessary to isolate (II), a second embodiment comprises the steps of chlorinating a compound having the formula

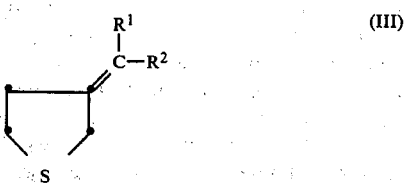

in an inert organic solvent under essentially anhydrous conditions to obtain (II) and then converting (II) to (I) by the means described above.

A third embodiment of the invention comprises a process for the preparation of (I) by contacting (II) with a base wherein a two-phase inert, organic solvent-water system is employed and the base is an amine soluble in the organic solvent and having a $pK_b$ of about 3–5.

The preparation of 3-thienylmalonic acid by a number of procedures is disclosed in U.S. Pat. No. 3,828,074; J.C.S. Perkin I, 2624 (1979); J.C.S. Chem. Comm., 500 (1979); and German Offen. No. 2,163,523. All of these published routes suffer from various disadvantages.

The compound of formula (III) in which $R^1$ is methoxycarbonyl and $R^2$ is cyano is known from the work of Gewald et al. (Journal f. Prakt. Chemie, 315, 39 (1973). The formula (III) compound in which $R^1$ and $R^2$ each is methoxycarbonyl can be prepared according to the procedure described in Tetrahedron, 29, 635 (1973). Compounds of formula (III) wherein $R^1$ and $R^2$ represent other groups, or combinations of groups, hydrolyzeable to carboxyl groups can be obtained from procedures analagous to those published in the literature.

Attempts to aromatize Compound (II) to Compound (I), which might appear simple in view of the state of the art, met with failure. See J. Org. Chem., 45, No. 4, 617 (1980). For example, chlorinating Compound (III) to obtain Compound (II) and treating the latter with sodium carbonate or triethylamine gave brown tars with very little, if any, of the desired product. Although I do not intend to limit the scope of the invention by any particular theory why known techniques for aromatizing compounds of formula (II) failed, it is my belief that the use of the stronger amines causes formation of anions having the formula

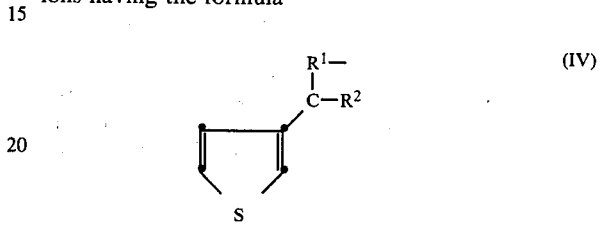

This anion is believed to react with (II) resulting in the formation of tars to the exclusion of the desired product. Thus, it is considered that the successful conversion of (II) to (I) requires that the formation of anion (IV) in the reaction medium be minimized or eliminated or, alternatively, that the contact between (IV) and (II) be avoided.

The first embodiment of the invention comprises the discovery that the use of an amine base having a $pK_b$ of about 8 to 10 is basic enough to cause reaction with compounds of formula (II) but is not basic enough to allow formation of anion (IV) and thus gives good yields of (I). Examples of the amines that may be used include pyridine, $C_1$–$C_4$ alkyl-substituted pyridines such as the picolines, the lutidines and 2-methyl-5-ethylpyridine, quinoline, $C_1$–$C_4$ alkyl-substituted quinolines such as 2- and 4-methylquinoline, 1,2-dihydro-2,2,4-trimethylquinoline, 2-isopropyl-6-methyltetrahydroquinoline, 2,2,4,6-tetrahydroquinoline, N,N-dialkylanilines and toluidines wherein the alkyl groups preferably are $C_1$–$C_4$ alkyl, etc. The most useful amines (cost-performance) are the pyridines, picolines, lutidines and mixtures thereof. A relatively inexpensive base that is useful is denaturing pyridine, a commercially available product consisting of less than 1% pyridine and about 48% 3- and 4-picolines, 17% 2,6-lutidine and 32% 2-picoline.

The groups represented by $R^1$ and $R^2$ are not necessarily directly hydrolyzable to a carboxyl group. For example, each group may be treated with a strong acid in an alkanol to first convert each to an alkoxycarbonyl group which then may be hydrolyzed to carboxyl groups by known means. Examples of the groups represented by $R^1$ and $R^2$ include cyano, 4,4-dimethyl-2-oxazolinyl or groups having the formula —$COOR^3$ and —$CONR^4R^5$ wherein $R^3$ is alkyl of up to about 4 carbon atoms and $R^4$ and $R^5$ are hydrogen or $R^3$. Preferably, $R^1$ is —$COOR^3$ and $R^2$ is cyano or —$COOR^3$.

The inert organic solvent employed in the reaction of (II) with an amine base can be selected from various hydrocarbons, chlorinated hydrocarbons, ethers, glycols, alkanols and alkyl esters of carboxylic acids and forms no part of the invention. Examples of such solvents include hydrocarbons and chlorinated hydrocarbons such as hexane, benzene, toluene, mixed xylenes, methylene chloride, chloroform, carbon tetrachloride, ethylene dichloride, mono- and dichlorobenzenes, tetrahydrofuran, di-$C_1$-$C_4$ alkylethers, $C_2$-$C_4$ -glycols such as ethylene, propylene and tetramethylene glycol, $C_1$-$C_4$ alkanols, methyl and ethyl acetate, etc. Since (II) normally will not be isolated, the solvent ordinarily will be one that is inert, or substantially inert, to the chlorination step by which (II) is prepared, e.g. the hydrocarbons, chlorinated hydrocarbons, ethers and esters described above. The reaction temperature can be varied widely, for example, from about $-5°$ to $50°$ C., although temperatures of about $0°$-$25°$ C. are preferred. In the first embodiment of the invention water is not normally used in conjunction with the inert organic solvent. However, water can be present although there is no advantage to its presence.

The mole ratio of base to (II) preferably is 1:1 or more. The use of excess base, e.g. up to about ten mole percent, is desirable since it speeds up the reaction and reacts with any HCl that remains from the chlorination step. Mole ratios of less than 1:1 can be used but yields of (I) obviously will suffer.

The second embodiment of my invention comprises monochlorinating (III) in an inert organic solvent to obtain a solution of (II) which then may be converted to (I) as described hereinabove. The monochlorination of (III), which is not in itself unique, is accomplished by treating (I) with a chlorinating agent such as chlorine or, preferably, sulfuryl chloride in an inert organic solvent such as those described above. A molar ratio of chlorinating agent to (I) of about 1:1 generally gives good results. Excess chlorinating agent should be avoided since some undesirable dichlorinated compound will be formed which causes purification difficulties. The chlorination temperature can be in the range of about $-5°$ to $50°$ C., preferably $0°$-$10°$ C.

The third embodiment of my invention comprises the use of a two phase reaction system consisting of an inert, water-immiscible organic solvent wherein (II), dissolved in the organic phase, is reacted with a tertiary amine that is soluble in the organic phase and has a $pK_b$ of about 3 to 5 to obtain a water-soluble intermediate and acidifying the aqueous phase to obtain (I). Examples of suitable organic solvents include hydrocarbons, chlorinated hydrocarbons, ethers and esters, e.g. the water-immiscible solvents mentioned above. If the only base employed in the reaction system is an amine soluble in the organic phase, the mole ratio of amine to (I) should be at least 1:1. Preferably, an excess of amine is used, e.g., up to 10 mole percent excess amine. Examples of suitable amines include trialkyl amines such as triethylamine, tributylamine, tricaprylamine and trilaurylamine, piperidine, N-ethylpiperidine, N,N,N',N'-tetraethyl ethylenediamine, hexamethylenetetramine, 1,4-diazabicyclo[2.2.2]octane, and tetraalkylammonium salts such as benzyltriethylammonium chloride and tetracapryl-ammonium bromide. The preferred amines are the trialkylamines containing a total of 12 or more carbon atoms which are substantially more soluble in the organic, rather than the aqueous, phase. Although amines, such as triethylamine, containing less than 12 carbon atoms possess substantial solubility in water, they are sufficiently soluble in organic solvents, especially when the two-phase reaction medium is being agitated, to effect reaction with (II) to form the water-soluble intermediate.

An alternative technique comprises the use of a catalytic amount of an amine base soluble in the organic phase and a stronger base, e.g. an inorganic base, that is water-soluble. Examples of the water-soluble bases include the alkali metal and ammonium carbonates and hydroxides. The catalytic amount of organic-soluble amine will be at least 0.001 mole per mole of (II) although higher ratios, e.g. 0.1 or more, will result in the more rapid formation of the water-soluble intermediate. The amount of water-soluble base used can vary, depending on the amount of amine base used. Generally, the mole ratio of water-soluble base to (II) will be at least 1:1, preferably about 1.1:1. The amounts and volume ratios of the inert, water-immiscible solvent to water can be varied substantially and in general, will depend on economic considerations.

The water-soluble intermediate present is converted to (I) by acidifying the aqueous phase to a pH of 7, preferably to a pH of 5. Suitable acids include sulfuric, hydrochloric, acetic, citric and phosphoric.

The process of the invention is further illustrated by the following examples.

EXAMPLE 1

A solution of 5.00 g (27.3 mmol) of methyl 2-cyano-2-(3-tetrahydrothienylidene)acetate in 100 ml of methylene chloride was cooled to $+5°$ under nitrogen and 3.70 g (27.3 mmol) of sulfuryl chloride in 5 ml of methylene chloride was added all at once. After 15 min. at $+5°$ the solution was purged with a vigorous stream of nitrogen for 5 min. Pyridine (4.0 g, 50 mmol, 1.83 eq.) was added and the solution was brought to room temperature with a water bath. After 30 min. the reaction was quenched with 30 ml of 1 M $H_2SO_4$ and 70 ml of water. The mixture was stirred to 15 min. and the organic phase was separated. The aqueous phase was extracted with 30 ml of methylene chloride and the combined organic layers were dried by passing them through a cone of anhydrous calcium sulfate. Solvent was removed to yield an orange oil homogeneous by tlc and glc (SE-30, SP2300). Bulb to bulb distillation (about $120°/0.5$ torr) yielded 4.67 g (94.5%) of methyl 2-cyano-2(3-thienyl)acetate as an analytically pure pale yellow oil, bp $108°$-$110°/0.5$ torr, (lit. $107°$-$9°/0.95$ torr). IR (film) 4.42 (w), 5.73 (s), 6.98 (m), 8.00 (s), 9.86 (m), 12.95 (s); NMR (CDCl$_3$) 7.6-7.4 (m, 2H), 7.3-7.1 (d×d, J=2, 5 Hz, 1H), 5.00 (s, 1H), 3.90 (s, 3H), UV max=234 nm. $^{13}$C NMR (CDCl$_3$) 165.0, 129.1, 127.5, 126.6, 124.7, 115.5, 53.9, 38.9.

Analysis: Calcd for $C_8H_7NO_2S$: C, 53.02; H, 3.89; N, 7.73; S, 17.70. Found: C, 53.28; H, 3.83; N, 7.79; S, 17.47.

EXAMPLE 2

Methyl 2-cyano-2-(2-chloro-3-tetrahydrothienylidene)acetate was prepared from 10.0 g of methyl 2-cyano-2-(3-tetrahydrothienylidene)acetate as described above. It was added, in 50 ml of toluene, over a period of 1 hour to a mixture of 23 g of 50% sodium hydroxide, 100 ml of water, 50 ml of toluene and 2 g of tributylamine in a 500 ml flask equipped with a stopcock at the bottom and a mechanical stirrer. The aqueous phase was added to 30 g of sulfuric acid in 200 ml of ice and water. Extraction with methylene chloride, drying with calcium sulfate and bulb-to-bulb distillation afforded 8.17 g of an oil consisting of methyl 3-thienylcyanoacetate and about 20% of 3-thienyl acetonitrile (glc-ms).

EXAMPLE 3

A solution of 0.50 g (2.31 mol) of dimethyl 2-(3-tetrahydrothienylidene)malonate in 10 ml of toluene was treated with 0.32 g (2.35 mmole) of sulfuryl chloride in 1 ml of toluene under nitrogen at ice bath temperature. The mixture turned dark, and starting material could not be observed by tlc after 5 min. Nitrogen was bubbled through the solution for 5 min., and the dark color faded. Pyridine (1 ml) was added. After 15 min. at room temperature, the solution was worked up as in Example 1 and molecular distillation gave 0.45 g (93%) of dimethyl 2-(3-thienylidene)malonate, containing minor impurities by glc (SE-30, 200°).

The invention has been described in detail with particular reference to certain preferred embodiments thereof, but it will be understood that variations and modifications can be effected within the spirit and scope of the invention. The particular temperatures, solvents, solvent:reactant ratios, reactant:reactant ratios, amine and inorganic bases, etc., that can be used in practicing the processes of the invention will be readily apparent, especially in view of the above disclosure, to those skilled in the art. Thus, those features should not be regarded as constituting a part of my invention in its broader, as opposed to preferred, aspects.

I claim:

1. Process for the preparation of a compound having the formula

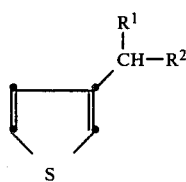

which comprises contacting a compound having the formula

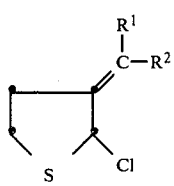

in an inert solvent with an amine having a $pK_b$ of about 8 to 10, wherein $R^1$ and $R^2$ are groups hydrolyzable to carboxyl groups.

2. Process according to claim 1 for the preparation of a compound having the formula

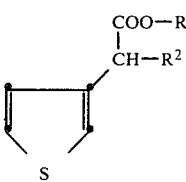

which comprises contacting a compound having the formula

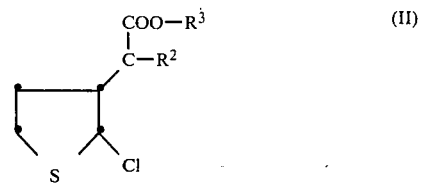

in an inert solvent at temperature of about $-5°$ to $50°$ C. with pyridine, one or more picoline, one or more lutidine or a mixture thereof, the mole ratio of amine to (II) being at least 1:1, wherein $R^2$ is cyano or $-COO-R^3$ and $R^3$ is $C_1-C_4$ alkyl.

3. A process according to claim 2 wherein the inert solvent is a hydrocarbon or chlorinated hydrocarbon and the temperature is about $0°$ to $25°$ C.

4. A process for the preparation of a compound having the formula

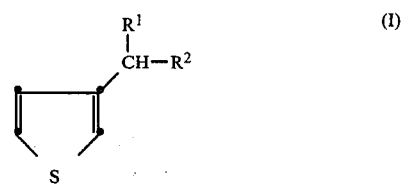

which comprises monochlorinating a compound having the formula

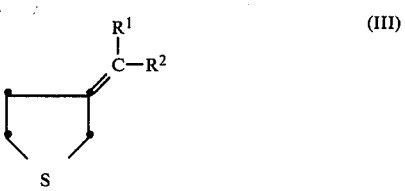

with a chlorinating agent in an inert solvent to obtain a compound having the formula

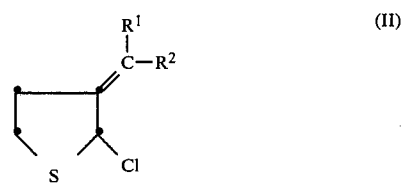

and contacting the compound of formula (II) in the inert solvent with an amine having a $pK_b$ of about 8 to 10, wherein $R^1$ and $R^2$ are groups hydrolyzable to carboxyl groups.

5. A process according to claim 4 for the preparation of a compound having the formula

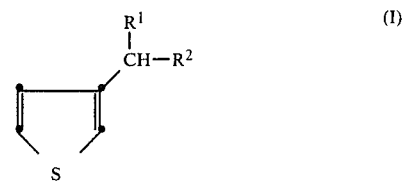

which comprises monochlorinating a compound having the formula

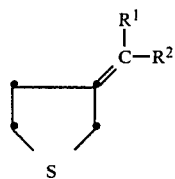
(III)

with chlorine or sulfuryl chloride in a chlorinated hydrocarbon solvent to obtain a compound having the formula

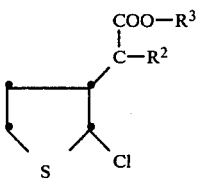
(II)

and contacting the compound of formula (II) in the chlorinated hydrocarbon solvent at a temperature of about −5° to 50° C. with pyridine, one or more picoline, one or more lutidine or a mixture thereof, the mole ratio of amine to (II) being at least 1:1, wherein $R^2$ is cyano or —COO—$R^3$ and $R^3$ is $C_1$-$C_4$ alkyl.

6. A process for the preparation of a compound having the formula

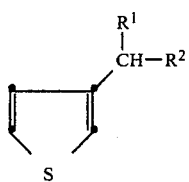
(I)

in a two-phase reaction system consisting of an inert, water-immiscible organic solvent and water which comprises contacting a compound having the formula

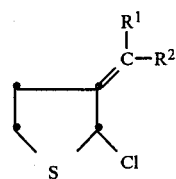
(II)

in the organic solvent with a tertiary amine that is soluble in the organic solvent and has a $pK_b$ of about 3 to 5 to obtain a water-soluble intermediate and acidifying the aqueous phase, wherein $R^1$ and $R^2$ are groups hydrolyzable to carboxyl groups.

7. Process according to claim 6 wherein a catalytic amount of amine is employed and the aqueous phase contains an alkali metal or ammonium carbonate or hydroxide.

* * * * *

UNITED STATES PATENT AND TRADEMARK OFFICE
CERTIFICATE OF CORRECTION

PATENT NO. : 4,307,239
DATED : December 22, 1981
INVENTOR(S) : Peter W. Raynolds It is certified that error appears in the above—identified patent and that said Letters Patent is hereby corrected as shown below:

Column 6, lines 1-9, the formula should be

--- (II) 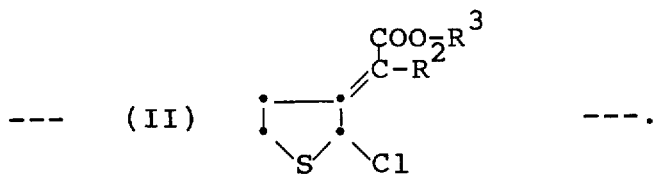 ---.

Column 7, lines 18-25, the formula should be

--- (II) 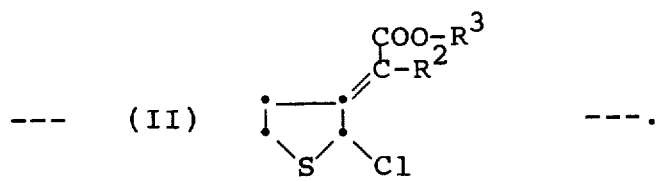 ---.

Signed and Sealed this

Sixteenth Day of March 1982

[SEAL]

Attest:

Attesting Officer

GERALD J. MOSSINGHOFF

Commissioner of Patents and Trademarks